(12) United States Patent
Turski et al.

(10) Patent No.: US 7,696,383 B2
(45) Date of Patent: Apr. 13, 2010

(54) N-OXIDES OF VENLAFAXINE AND O-DESMETHYLVENLAFAXINE AS PRODRUGS

(75) Inventors: Lechoslaw A. Turski, Weesp (NL); Axel Stoit, Weesp (NL); Cornelis G. Kruse, Weesp (NL); Sander Vader, Weesp (NL); Martinus Th. M. Tulp, Weesp (NL)

(73) Assignee: Solvay Pharmaceuticals B.V., Weesp (NL)

( * ) Notice: Subject to any disclaimer, the term of this patent is extended or adjusted under 35 U.S.C. 154(b) by 0 days.

(21) Appl. No.: 12/143,919

(22) Filed: Jun. 23, 2008

(65) Prior Publication Data

US 2009/0005455 A1    Jan. 1, 2009

Related U.S. Application Data

(60) Provisional application No. 60/946,200, filed on Jun. 26, 2007.

(51) Int. Cl.
*C07C 291/04* (2006.01)
*A61K 31/13* (2006.01)

(52) U.S. Cl. ............... 564/299; 564/298; 514/644

(58) Field of Classification Search ............ None
See application file for complete search history.

(56) References Cited

U.S. PATENT DOCUMENTS 4,252,951 A * 2/1981 Jackson et al. ............ 540/220
2008/0261895 A1 * 10/2008 Hoffmann et al. .......... 514/25

OTHER PUBLICATIONS

Braga et al., Chem. Commun. (2005), 29, p. 3635-3645.*

* cited by examiner

*Primary Examiner*—Brian J Davis
(74) *Attorney, Agent, or Firm*—Finnegan, Henderson, Farabow, Garrett & Dunner, L.L.P.

(57) ABSTRACT

Embodiments of the invention relate to a compound of formula (1),

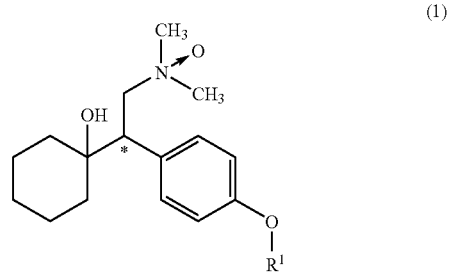

or a tautomer, stereoisomer, hydrate, or solvate thereof, wherein $R^1$ is H or $CH_3$. Other embodiments of the invention relate to a pharmaceutical composition containing these compound, to methods for preparing these compounds, and to methods for preparing compositions containing these compounds. Yet other embodiments of the invention relate to the uses of these compounds and compositions containing it, such as for the manufacture of medicaments and pharmaceutical compositions for treating a condition chosen from depression, major depressive disorder, generalized anxiety disorder, obsessive compulsive disorder, social anxiety disorder, panic disorder, general depressive disorders, diabetic neuropathy, migraine and hot flashes.

11 Claims, No Drawings

N-OXIDES OF VENLAFAXINE AND O-DESMETHYLVENLAFAXINE AS PRODRUGS

This application claims the benefit of priority of U.S. Provisional Application No. 60/946,200, filed on Jun. 26, 2007, the disclosure of which is incorporated herein by reference.

This invention relates to the fields of pharmaceutical and organic chemistry. Embodiments of the present invention relate to venlafaxine-N-oxide and O-desmethylvenlafaxine-N-oxide compound, of formula (1):

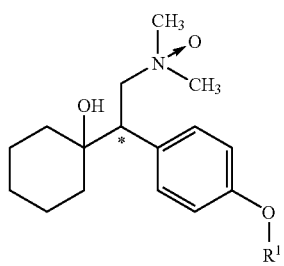

(1)

or a tautomer, stereoisomer, hydrate or solvates thereof, wherein the asterisk (*) marks the asymmetric carbon atom, and wherein $R^1$ is H or $CH_3$. The compounds of formula (1) are prodrugs of venlafaxine and its major (active) metabolite O-desmethylvenlafaxine respectively. Other embodiments of the present invention relate to pharmaceutical compositions comprising a compound of formula (1), methods for preparing a compound of formula (1), and methods for preparing compositions comprising a compound of formula (1).

Venlafaxine is a phenethylamine bicyclic derivative, chemically unrelated to tricyclic, tetracyclic or other available antidepressant agents. It has been reported that its (−)-enantiomer is a more potent inhibitor of norepinephrine synaptosomal uptake while its (+)-enantiomer is more selective in inhibiting serotonin uptake (Howell, 1994). Venlafaxine is marketed as a racemate:

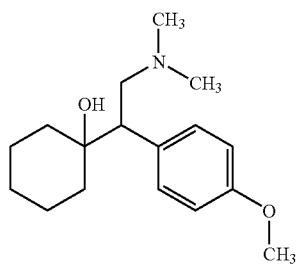

(±)-1-[2-(dimethylamino)-1-(4-methoxyphenyl)ethyl]-cyclohexanol,
venlafaxine
(U.S. Pat. No. 4,761,501; Pento, 1988)

The mechanism of venlafaxine's antidepressant action in humans is believed to be associated with its potentiation of neurotransmitter activity in the central nervous system (CNS). Preclinical studies have shown that venlafaxine and its major metabolite, O-desmethylvenlafaxine, are potent inhibitors of neuronal serotonin and norepinephrine reuptake and weak inhibitors of dopamine reuptake. O-desmethylvenlafaxine is the only major active metabolite. Other metabolites are N-desmethylvenlafaxine, and N,O-didesmethylvenlafaxine (Klamerus, 1992). O-desmethylvenlafaxine succinate is in a late stage of its development, and recently received an approvable letter from the FDA for the treatment of Major Depressive Disorder. The compound is also in development as treatment of vasomotor symptoms associated with menopause.

N-oxides have been known since 1894. By now it is very well known that N-oxides are metabolites of many tertiary amines, and in most cases are also intermediates between tertiary amines and their N-dealkylated analogs. Most, but not all, tertiary amine drugs give rise to N-oxides. This is the case with morphine, imipramine, promazine, cinnarizine and nicotine. The amount of N-oxidation that occurs varies from trace amounts to a nearly quantitative conversion. Some N-oxides were shown to be more potent than their corresponding tertiary amines. The most famous example of these is chlordiazepoxide (Librium®), one of the most frequently used drugs in psychiatric and general medicine. In many more cases however, N-oxides were found to be less potent than their corresponding tertiary amines, and N-oxidation is most commonly regarded to be metabolic deactivation. While N-oxides are easily reduced to their corresponding tertiary amines by chemical means, in the human body this conversion occurs in varying degrees. Some N-oxides undergo nearly quantitative reductive conversion to their corresponding tertiary amines and in other cases the conversion is a mere trace reaction or even completely absent (Bickel, 1969). Thus, the formation of N-oxides and their corresponding tertiary amines is unpredictable. N-oxides may or may not be reduced to their corresponding tertiary amines. When N-oxides are converted to their corresponding tertiary amines, the conversion may be in mere trace amounts or nearly quantitative. Once formed, N-oxides may be more active than their corresponding tertiary amines, less active or even completely inactive. N-oxides may be reduced to the corresponding tertiary amines or not. When they are, the reaction may be a mere trace or nearly quantitative.

It is generally accepted that therapeutic as well as toxic effects of drugs are related to their concentration at the relevant target sites. Because generally speaking the latter are not easily accessible, blood plasma levels are used as approximations of relevant drug concentrations. During drug development a window of suitable plasma concentrations are defined providing a lower limit or range for efficacy, and an upper range at which side effects start to become apparent. In ideal situations, the two concentrations are so far apart that it is easy to administer the drug in such a way that it is effective, yet does not give rise to side effects. In reality, situations are hardly ever ideal, and most drugs show side effects. In most cases, the occurrence of side effects can be linked to peak plasma concentrations exceeding the lower level associated with the occurrence of side effects. Venlafaxine produces peak plasma concentrations resulting in side effects. The most commonly observed adverse events associated with the use of venlafaxine (incidence of 5% or greater) and not seen at an equivalent incidence among placebo-treated patients (i.e., incidence for venlafaxine at least twice that for placebo), include sustained hypertension, headache, asthenia, sweating, nausea, constipation, somnolence, dry mouth, dizziness, insomnia, nervousness, anxiety, blurred or blurry vision, and abnormal ejaculation/orgasm or impotence in males (*Physicians' Desk Reference,* 1999; Sinclair, 1998). These adverse effects can significantly limit the dose level, frequency, and duration of drug therapy. Adverse events can be attenuated using extended-release formulations (venlafaxine XR), but different compounds can solve the problem, too.

The objective of the present invention is to find a compound with the advantages of venlafaxine while avoiding its

DESCRIPTION

It was found that venlafaxine-N-oxide and O-desmethyl-venlafaxine-N-oxide, compounds of formula (1), act as prodrugs, and when they are administered orally, they are rapidly converted to their parent compounds venlafaxine and O-desmethyl-venlafaxine, respectively. Embodiments of the invention relate to N-oxides of formula (1):

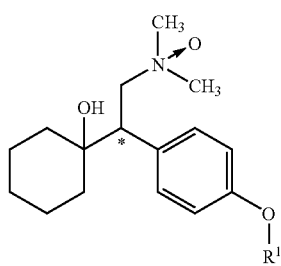

or a tautomer, stereoisomer, hydrate or solvate thereof, wherein the asterisk (*) marks the asymmetric carbon atom, and wherein $R^1$ is H or $CH_3$. In some embodiments, the invention relates to a compound of formula (1), which may be substantially free of venlafaxine and O-desmethylvenlafaxine, or a tautomer, stereoisomer, salt, hydrate or solvate thereof. Venlafaxine N-oxide and O-des-methylvenlafaxine N-oxide can be prepared by oxidizing venlafaxine or O-desmethylvenlafaxine with a suitable oxidizing agent, for instance with m-CPBA. In other embodiments, the invention relates to racemates, mixtures of diastereomers and the individual stereoisomers of compounds of formula (1), as well as to hydrates and solvates thereof.

In one embodiment, the invention relates to a compound of formula (1) wherein $R^1$ is $CH_3$.

In another embodiment, the invention relates to a compound of formula (1) wherein $R^1$ is H.

In yet other embodiments, the invention relates to (S)- and (R)-enantiomers of compounds of formula (1).

Venlafaxine-N-oxide compounds and compositions comprising these compounds are useful in treating conditions or diseases effectively treatable—albeit with side effects—with venlafaxine such as depression, including major depressive disorder, generalized anxiety disorder, obsessive compulsive disorder, social anxiety disorder, panic disorder, general depressive disorders, diabetic neuropathy, migraine and vasomotor symptoms associated with menopause, also known as "hot flashes."

Other embodiments of the invention include, but are not limited to:

pharmaceutical compositions for treating, for example, a disorder or condition treatable by venlafaxine, the compositions comprising a compound of formula (1) or a tautomer, stereoisomer, hydrate, or solvate thereof, and at least one pharmaceutically acceptable carrier and/or at least one pharmaceutically acceptable auxiliary substance;

methods of treating a disorder or condition treatable by venlafaxine, the method comprising administering to a human or animal patient in need of such treating, a compound of formula (1) or a tautomer, stereoisomer, hydrate, or solvate thereof;

The invention also provides the use of a compound of formula (1) for the manufacture of medicament or a pharmaceutical composition.

The invention further relates to combination therapies comprising a compound of formula (1), or a pharmaceutical composition or formulation comprising a compound of formula (1), is administered concurrently or sequentially or as a combined preparation with another therapeutic agent or agents, for instance venlafaxine or O-desmethyl-venlafaxine, for treating one or more of the conditions listed herein. Such other therapeutic agent(s) may be administered prior to, simultaneously with, or following the administration of the compounds of the invention.

Embodiments of the invention also provides compounds, pharmaceutical compositions, kits and methods for treating a disorder or condition treatable by venlafaxine, the method comprising administering to a patient in need of such treating an N-oxide of formula (1) or a tautomer, stereoisomer, hydrate, or solvate thereof.

Embodiments of the invention also provide methods of preparing the compounds of the invention and the intermediates used in those methods.

In some embodiments, the compounds of the present invention contain an asymmetric center. This will produce two optical isomers. All of the possible optical isomers and diastereomers, in mixtures and as pure or partially purified compounds, are within the scope of this invention. The present invention comprehends all such isomeric forms of these compounds. Formula (1) shows the structure of the class of compounds without preferred stereochemistry. The independent syntheses of these diastereomers, or their chromatographic separations, may be achieved as known in the art by appropriate modification of the methodology disclosed therein. Their absolute stereochemistry may be determined by the X-ray crystallography of crystalline products or crystalline intermediates, which are derivatized, if necessary, with a reagent containing an asymmetric center of known absolute configuration. Racemic mixtures of the compounds can be separated into the individual enantiomers by methods well-known in the art, such as the coupling of a racemic mixture of compounds to an enantiomerically pure compound to form a diastereomeric mixture, followed by separation of the individual diastereomers by standard methods, such as fractional crystallization or chromatography. The diasteromeric derivatives may then be converted to the pure enantiomers by cleavage of the added chiral residue. The racemic mixture of the compounds can also be separated directly by chromatographic methods utilizing chiral stationary phases, which are well-known in the art. Alternatively, any enantiomer of a compound may be obtained by stereoselective synthesis using optically pure starting materials or reagents of known configuration by methods well-known in the art.

Some of the crystalline forms for the compounds may exist as polymorphs, and as such are intended to be included in the invention. In addition, some of the compounds may form solvates with water (i.e., hydrates), or common organic solvents. Such solvates also fall within the scope of this invention.

Isotopically-labeled N-oxides of formula (1), detectable by PET or SPECT, also fall within the scope of the invention. The same applies to N-oxides of formula (1) labeled with [$^{13}$C]—, [$^{14}$C]—, [$^{3}$H]—, [$^{18}$F]—, [$^{125}$I]— or other isotopically enriched atoms for receptor binding or metabolism studies.

Discovering that N-oxides of venlafaxine and O-desmethylvenlafaxine are useful as prodrugs of their respective parent compounds, offers possibilities to use these compounds as alternatives, with the clinical benefits of an extended duration of action and a blunted peak plasma concentration, leading to an enhanced side-effect profile. Thus in some embodiments of the present invention, compounds of the present invention may be provided substantially free of parent compound, venlafaxine, 1-[2-(dimethylamino)-1-(4-methoxyphenyl)ethyl]-cyclohexanol, or O-desmethylvenlafaxine. Within the context of the present invention, substantially free means that compound of the present invention contains less than about 50%, 40%, 30%, 20%, 10%, 1%, 0.5% or is, within detectable limits, free of venlafaxine or O-desmethylvenlafaxine, as an impurity. Pharmaceutical compositions comprising N-oxides of venlafaxine and/or O-desmethylvenla-faxine which are substantially free of venlafaxine and/or O-desmethylvenlafaxine are within the scope and spirit of the present invention.

Definitions

As used herein, the term "venlafaxine" means the racemic compound (R,S)-1-[2-(dimethylamino)-1-(4-methoxyphenyl)ethyl]cyclohexanol.

Any compound metabolized in vivo to provide the bioactive agent (i.e., the compound of formula (1)) is a prodrug within the scope and spirit of the application. Prodrugs are therapeutic agents, inactive per se, but transformed into one or more active metabolites. Thus, in the methods of treatment of the present invention, the term "administering" shall encompass treating the various disorders described with the compound specifically disclosed, or with a compound that not specifically disclosed, but that converts to the specified compound in vivo after administration to the patient. Prodrugs are bioreversible derivatives of drug molecules used to overcome some barriers to the utility of the parent drug molecule. These barriers include, but are not limited to, solubility, permeability, stability, presystemic metabolism and targeting limitations (Bundgaard, 1985; King, 1994; Stella, 2004; Ettmayer, 2004; Järvinen, 2005). Prodrugs, i.e., compounds that when administered to humans by any known route, are metabolized to compounds having formula (1), belong to the invention. For example, this relates to the hydroxy group, which can be reacted with organic acids to yield compounds having formula (1) wherein an additional group is present that is easily removed after administration, for instance, but not limited to amidine, enamine, a Mannich base, a hydroxyl-methylene derivative, an O-(acyloxymethylene carbamate) derivative, carbamate, ester, amide or enaminone.

The term "polymorphism" is defined as the ability of a compound to exist in more than one crystal form, a so-called polymorph. Polymorphism is a frequently occurring phenomenon. Polymorphism is affected by several crystallization conditions such as temperature, level of supersaturation, the presence of impurities, polarity of solvent, rate of cooling. Polymorphs can be characterized by several methods such as solid state NMR, solubility tests, DSC or melting point determination, IR or Raman spectroscopy.

To provide a more concise description, some of the quantitative expressions given herein are not qualified with the term "about". It is understood that whether the term "about" is used explicitly or not, every quantity given herein is meant to refer to the actual given value, and it is also meant to refer to the approximation to such given value that would reasonably be inferred based on the ordinary skill in the art, including approximations due to the experimental and/or measurement conditions for such given value. Throughout the description and the claims of this specification the word "comprise" and variations of the word, such as "comprising" and "comprises" is not intended to exclude other additives, components, integers or steps. The term "composition" as used herein encompasses a product comprising specified ingredients in predetermined amounts or proportions, as well as any product that results, directly or indirectly, from combining specified ingredients in specified amounts. In relation to pharmaceutical compositions, this term encompasses a product comprising one or more active ingredients, and an optional carrier comprising inert ingredients, as well as any product that results, directly or indirectly, from combination, complexation or aggregation of any two or more of the ingredients, or from dissociation of one or more of the ingredients, or from other types of reactions or interactions of one or more of the ingredients. In general, pharmaceutical compositions are prepared by uniformly and intimately bringing the active ingredient into association with a liquid carrier or a finely divided solid carrier or both, and then, if necessary, shaping the product into the desired formulation. The pharmaceutical composition includes enough of the active object compound to produce the desired effect upon the progress or condition of diseases. Accordingly, the pharmaceutical compositions of the present invention encompass any composition made by admixing a compound of the present invention and a pharmaceutically acceptable carrier.

Within the context of this application, the term "combination preparation" comprises both true combinations, meaning an N-oxide of formula (1), and other medicaments physically combined in one preparation such as a tablet or injection fluid, as well as "kit-of-parts," comprising an N-oxide of formula (1), and venlafaxine or another medicament in separate dosage forms, together with instructions for use, optionally with further means for facilitating compliance with the administration of the component compounds, e.g. label or drawings. With true combinations, the pharmacotherapy by definition is simultaneous. The contents of "kit-of-parts," can be administered either simultaneously or at different time intervals. Therapy being either concomitant or sequential will be dependant on the characteristics of the other medicaments used, characteristics like onset and duration of action, plasma levels, clearance, etc., as well as on the disease, its stage, and characteristics of the individual patient.

By "pharmaceutically acceptable" it is meant the carrier, diluent or excipient must be compatible with the other ingredients of the formulation and not deleterious to the recipient thereof.

Dose, as used herein, is the same as the recommended treatment dose for venlafaxine, 75 mg per day, administered in two or three divided doses, taken with food. Pharmacokinetic, pharmacodynamic, and other considerations may alter the dose actually administered to a higher or lower value. The dose of the compound to be administered will depend on the relevant indication, the age, weight and sex of the patient and may be determined by a physician. The dosage will be in the range of from 0.01 mg/kg to 10 mg/kg. The typical daily dose of the active ingredients varies within a wide range and will depend on various factors such as the relevant indication, the route of administration, the age, weight and sex of the patient and may be determined by a physician. In general, oral and parenteral dosages will be in the range of 0.1 to 1,000 mg per day of total active ingredients.

The term "therapeutically effective amount" as used herein refers to an amount of a therapeutic agent to treat or prevent a condition treatable by administrating a composition of the invention. That amount is the amount sufficient to exhibit a detectable therapeutic, preventative or ameliorative response in a tissue system, animal or human. The effect may include, for example, treating or preventing the conditions listed herein. The precise effective amount for a subject will depend upon the subject's size and health, the nature and extent of the condition being treated, recommendations of the treating physician (researcher, veterinarian, medical doctor or other clinician), and the therapeutics, or combination of therapeutics, selected for administration. Thus, it is not useful to specify an exact effective amount in advance.

The term "treatment" as used herein refers to any treatment of a mammalian, preferably human condition or disease, and includes: (1) preventing the disease or condition from occurring in a subject predisposed to the disease, but not yet diagnosed as having it, (2) inhibiting the disease or condition, i.e., arresting its development, (3) relieving the disease or condition, i.e., causing the condition to regress, or (4) stopping the symptoms of the disease. As used herein, the term "medical therapy" intendeds to include prophylactic, diagnostic and therapeutic regimens carried out in vivo or ex vivo on humans or other mammals. The term "subject" as used herein, refers to an animal, for example a mammal, such as a human, who has been the object of treatment, observation or experiment.

EXAMPLE 1

Analytical Methods

Nuclear magnetic resonance spectra ($^1$H NMR and $^{13}$C NMR, APT) were determined in the indicated solvent using a Bruker DRX 600 ($^1$H: 600 MHz, $^{13}$C: 150 MHz) at 300 K, unless indicated otherwise. The spectra were determined in deuterated DMSO, obtained from Cambridge Isotope Laboratories Ltd. Chemical shifts ($\delta$) are given in ppm downfield from tetramethylsilane ($^1$H). Coupling constants J are given in Hz. Peakshapes in the NMR spectra are indicated with the symbols 'q' (quartet), 'dq' (double quartet), 't' (triplet), 'dt' (double triplet), 'd' (doublet), 'dd' (double doublet), 's' (singlet), 'bs' (broad singlet) and 'm' (multiplet). NH and OH signals were identified after mixing the sample with a drop of $D_2O$.

Melting points were recorded on a Büchi B-545 melting point apparatus.

Flash chromatography refers to purification using the indicated eluent and silica gel (either Acros: 0.030-0.075 mm or Merck silica gel 60: 0.040-0.063 mm).

Reactions were monitored by using thin-layer chromatography (TLC) on silica coated plastic sheets (Merck precoated silica gel 60 F254) with the indicated eluent. Spots were visualised by UV light (254 nm) or $I_2$.

Liquid Chromatography-Mass Spectrometrry (LC-MS) was performed using a system consisting of 2 Perkin Elmer series 200 micro pumps. The pumps were connected to each other by a 50 µl tee mixer, connected to a Gilson 215 auto sampler. The method was as follows:

| step | total time | flow (µl/min) | A(%) | B(%) |
|---|---|---|---|---|
| 0 | 0 | 2000 | 95 | 5 |
| 1 | 1.8 | 2000 | 0 | 100 |
| 2 | 2.5 | 2000 | 0 | 100 |
| 3 | 2.7 | 2000 | 95 | 5 |
| 4 | 3.0 | 2000 | 95 | 5 |

A = 100% Water with 0.025% HCOOH and 10 mmol NH$_4$HCOO pH = +/−3
B = 100% ACN with 0.025% HCOOH The auto sampler had a 2 µl injection loop. The auto sampler was connected to a Waters Atlantis C18 30*4.6 mm column with 3 µm particles. The column was thermo stated in a Perkin Elmer series 200 column oven at 40° C. The column was connected to a Perkin Elmer series 200 UV meter with a 2.7 µl flowcel. The wavelength was set to 254 nm. The UV meter was connected to a Sciex API 150EX mass spectrometer. The mass spectrometer had the following parameters:

Scan range:150-900 a.m.u.; polarity: positive; scan mode: profile; resolution Q1: UNIT; step size: 0.10 a.m.u.; time per scan: 0.500 sec; NEB: 10; CUR: 10 IS: 5200; TEM: 325; DF: 30; FP: 225 and EP: 10. The light scattering detector was connected to the Sciex API 150. The light scattering detector was a Sedere Sedex 55 operating at 50° C. and 3 bar $N_2$. The complete system was controlled by a G3 powermac.

Venlafaxine and its N-oxide were analyzed in mouse plasma and brain samples using a generic bioanalytical method comprising protein precipitation and HPLC with MS/MS detection.

Proteins in 100 µl plasma were precipitated with acetonitrile, and 5 µl samples of the obtained solutions were analyzed. Complete brains were homogenized and centrifuged, and 10 µl samples of the supernatant were analyzed.

Liquid Chromatography-Tandem Mass Spectrometry (LC-MS/MS) was performed using a Sciex API4000 LC-MS/MS. Samples were quantified using extracted calibration samples, treated the same as the study samples, in the range of 1-5000 ng/ml and 5.0-5000 ng/brain for plasma and brain samples, respectively. Compound peak area was used for quantification. Calibration curves were fitted to the model $y=A+Bx+Cx^2$ (y is the peak area of the analyte, x is the nominal calibration level in ng/ml (plasma) or ng/g (brain), A is the intercept, B is the slope and C is the description of the curvature). $1/x^2$ weighing was used. LC-MS/MS system performance was monitored using a reference solution injected at standard intervals. The method was not validated in detail, therefore the reported concentrations were good estimations. The Lower Limit Of Quantification (LLOQ) was established at 1.00 ng/ml and 5.00 ng/brain, for plasma and brain samples, respectively. Values below the LLOQ were given as best estimate. Reversed phase HPLC was performed using gradient elution by a Hypersil BDS C18 100×4.6 mm 3 µm analytical column, at 45° C. and with a flow of 1.00 ml/min:

| | Solvent | | | |
|---|---|---|---|---|
| Time (min) | % A | % B | % C | % D |
| 0.00 | 10.0 | 70.0 | 0.0 | 20.0 |
| 1.00 | 10.0 | 70.0 | 0.0 | 20.0 |
| 2.00 | 10.0 | 10.0 | 0.0 | 80.0 |
| 4.00 | 10.0 | 10.0 | 0.0 | 80.0 |
| 4.10 | 10.0 | 70.0 | 0.0 | 20.0 |
| 7.00 | 10.0 | 0.0 | 0.0 | 20.0 |

Solvent A 100 mM NH$_4$FA/1% FA
Solvent B Milli-Q water
Solvent C methanol
Solvent D acetonitrile Detection on MS/MS was done using positive MRM ionization. Measured ions were:

| | venlafaxine | venlafaxine-N-oxide |
|---|---|---|
| Q1 | 278.3 | 294.5 |
| Q3 | 121.1 | 121.1 |

EXAMPLE 2

Syntheses of Specific Compounds (R,S)-1-[2-(dimethylamino)-1-(4-methoxyphenyl)ethyl]-cyclohexanol (venlafaxine), and (R,S)-1-[2-(dimethylamino)-1-(4-hydroxyphenyl)ethyl]-cyclohexanol (O-desmethylvenla-faxine) were synthesized as described in EP 1 721 889. An alternative to the latter is given below.

(R,S)-1-[2-oxido-(dimethylamino)-1-(4-methoxyphenyl)ethyl]-cyclohexanol (venlafaxine N-oxide) was prepared as follows:

Venlafaxine (0.28 g, 1.02 mmol) was dissolved in 20 ml DCM and cooled to −10° C. To the reaction mixture was added meta-chloroperbenzoic acid (m-CPBA, 0.8 g, 2.02 mmol) and the solution was stirred at −10° C. for 30 minutes. Solid $K_2CO_3$ (2 g) was added and the resulting mixture was stirred for another 30 minutes at 0< C. The reaction mixture was filtrated (glass funnel), and the precipitate was washed carefully with DCM. The resulting solution was concentrated and purified by flash chromatography ($SiO_2$, DCM/MeOH (95/5 followed by 9/1) to yield the title compound as a solid (0.22 g, 74%). mp 145° C. LCMS; $R_t$: 1.12 min, ([M+H]$^+$= 294). $^1$H-NMR (600 MHz, $D_6$DMSO): δ 7.12 (bd, J=8 Hz, 2H), 6.86 (bd, J=8 Hz, 2H), 3.95-3.89 (m, 1H), 3.73 (s, 3H), 3.56-3.52 (m, 1H), 3.28-3.25 (m, 1H), 3.14 (s, 3H), 2.95 (s, 3H), 1.69-1.53 (m, 3H), 1.47-1.42 (m, 1H), 1.38-1.32 (m, 2H), 1.31-1.25 (m, 1H), 1.02 (dt, J=11 Hz, 4 Hz, 1H), 0.87 (dt, J=11 Hz, 4 Hz, 1H), 0.77-0.69 (m, 1H).

(R,S)-1-[2-oxido-(dimethylamino)-1-(4-hydroxyphenyl)ethyl]-cyclohexanol (O-desmethyl-venlafaxine N-oxide) can be prepared by the same method.

(S)- and (R)-enantiomers of venlafaxine, their respective N-oxides, and the O-desmethyl analogues were synthesized as depicted in the scheme below.

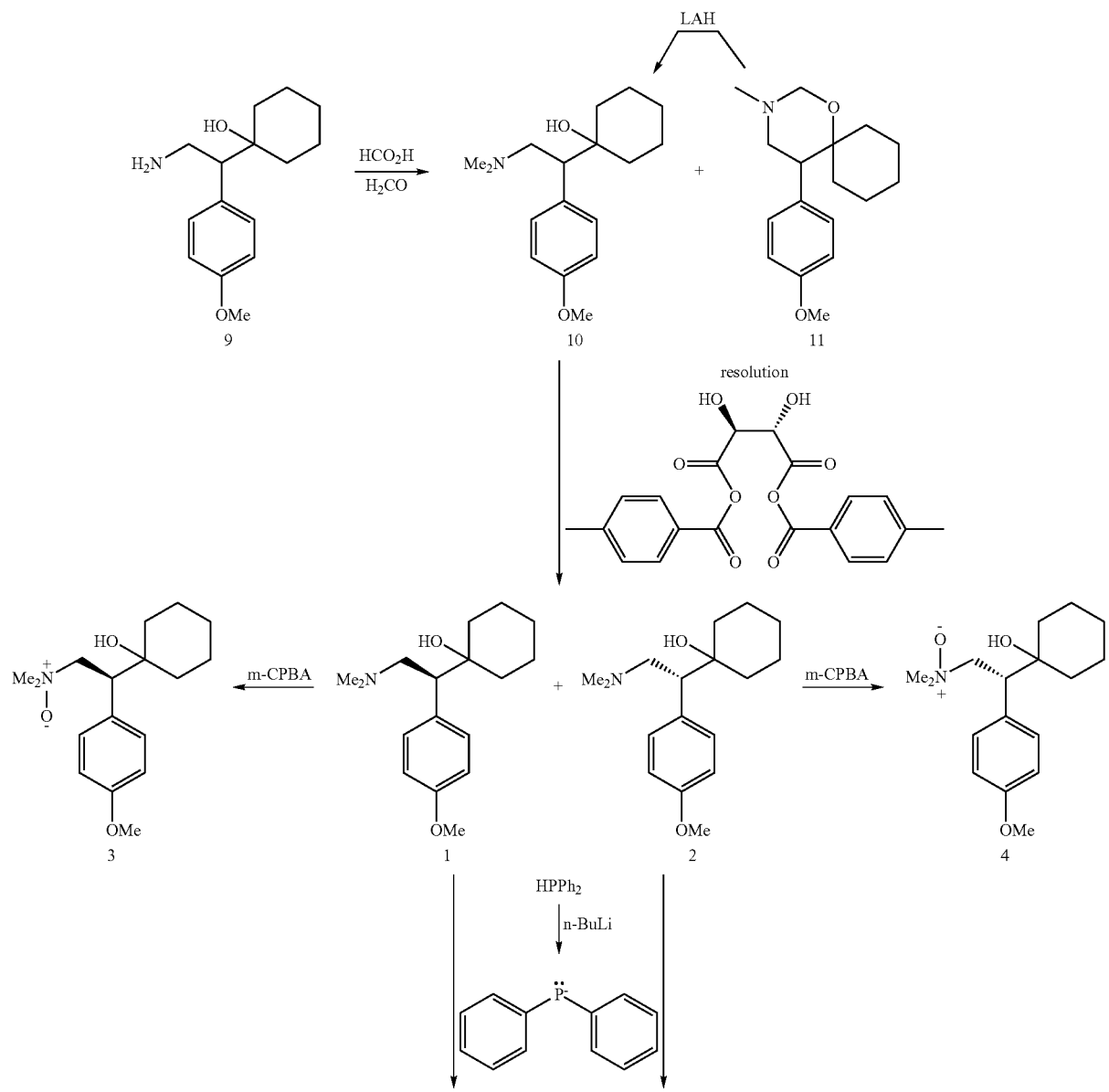

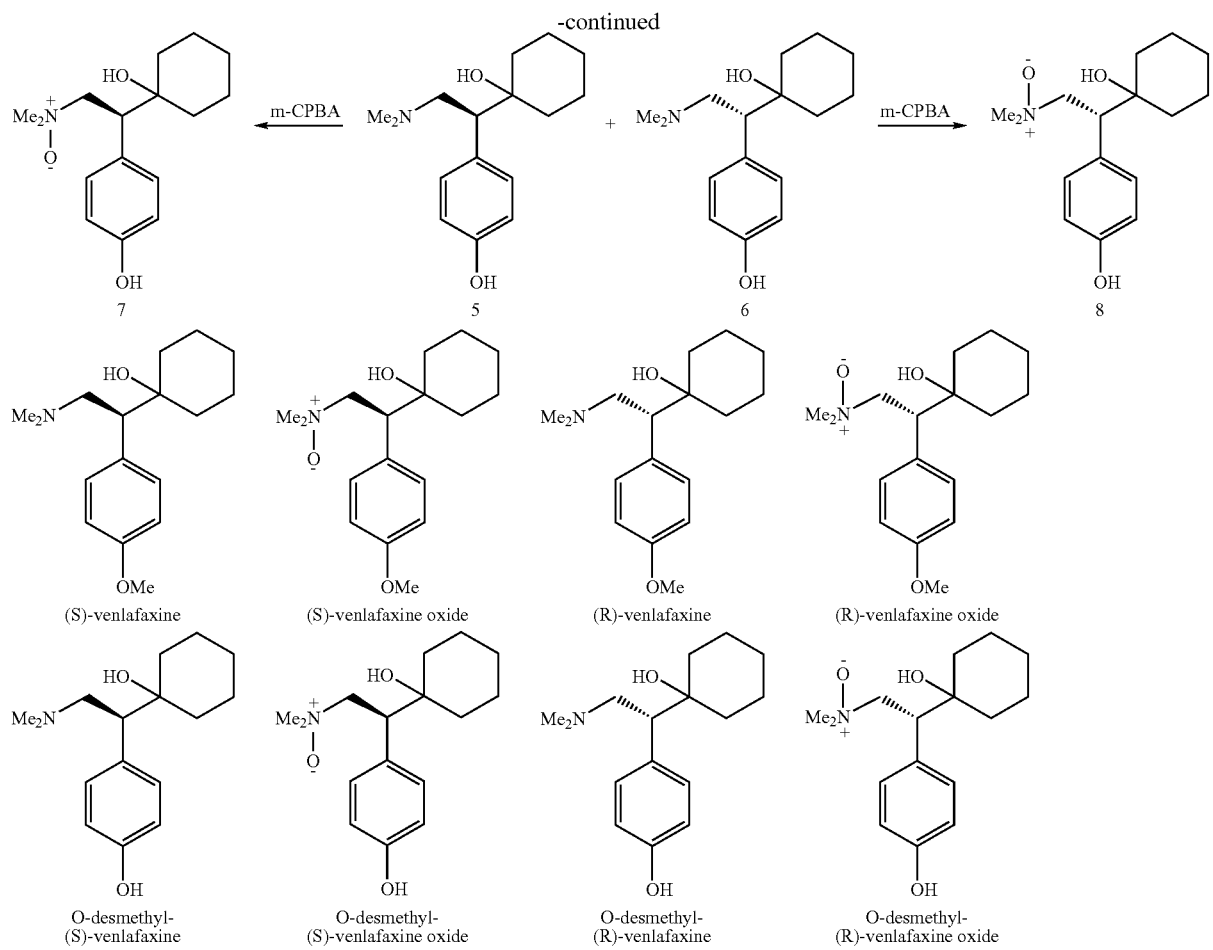

(R,S)-1-(2-(Dimethylamino)-1-(4-methoxyphenyl)ethyl) cyclohexanol (venlafaxine, compound 10) was prepared as follows:

Cyclohexanol (33 g, 0.13 mol) was dissolved in formic acid (99%, 54 mL, 1.43 mol) and water (330 mL) by addition of formaldehyde (37%, 41 mL, 1.48 mol). The mixture was refluxed for 2 h. Reaction mixture was concentrated to 150 mL (pH ~1.0), water (100 ml) was added and the mixture was extracted with ethyl acetate (4×100 mL). The aqueous layer was cooled in an ice bath and basified to pH ~10 by addition of 50% NaOH. The mixture was extracted with ethyl acetate (3×100 mL), dried over $Na_2SO_4$ and concentrated.

This material (23.8 g, mainly compound 11) was suspended in diethyl ether (500 mL) and treated with lithium aluminum hydride (3.8 g, 0.1 mol). The suspension was stirred for 18 h at rt. 5 N KOH (16 mL) was added carefully, and the mixture was stirred for 15 min. Solids were removed by filtering over Celite, and washed (diethyl ether, 300 mL). The filtrates were dried (sodium sulfate) and concentrated. Yield: 21.4 g of compound 10 (60 %) as a white solid. $^1$H-NMR (300 MHz, $CDCl_3$): δ 7.05 (d, 2H, J=8.8 Hz), 6.81 (d, 2H, J=8.8 Hz), 3.79 (s, 3H), 3.27 (t, 1H, J=12.6), 2.93 (dd, 1H, $^2$J=3.2 Hz, $^3$J=12.5 Hz), 2.32 (s, 6H), 2.30 (dd, 1H, $^2$J=3.2 Hz, $^3$J 12.5 Hz), 1.82-1.61 (m, 3H), 1.60-1.45 (m, 3H), 1.42-1.22 (m, 2H), 1.01-0.78 (m, 2H).

R-venlafaxine (compound 2 in the scheme above) was prepared as follows:

(R,S)-Venlafaxine (23.4 g, 84 mmol) was dissolved in ethyl acetate (160 mL). To the solution was added a solution of D-ditoluyl-tartaric acid (18.7 g, 48 mmol) in ethyl acetate (130 mL). Within 10 min. the salt started to precipitate. The mixture was stirred for 4 hours at room temperature. The precipitate was collected by filtering over a glass filter, and washed with ethyl acetate (2×100 mL) to obtain a white crystalline solid. This solid was recrystallized from ethyl acetate:methanol (6:1, 100 mL). The solids were collected on a glass filter. Yield: 14.0 g. This material was treated with 2N NaOH (cold, 180 mL). The aqueous phase was extracted with ethyl acetate (3×200 mL). The organic phase was washed with 2 N NaOH (cold, 75 mL) then with water until washings were neutral (pH 7). The organic phase was dried (sodium sulfate) and concentrated. Yield: 8.1 g of R-Venlafaxine (compound 2) as white crystalline solid. m.p.: 106° C.-109.5° C. $[α]_D^{23}$=−8.0 (c=1.5, MeOH). Chiral HPLC: 99% e.e. $^1$H-NMR ($CDCl_3$): see above.

S-Venlafaxine (compound 1) was prepared as follows:

The mother liquor of the resolution (see above) was freed by washing with 1 N NaOH (4×100 mL), with water (3×200 mL) and with brine (100 mL). The organic phase was dried (sodium sulfate) and concentrated. Oil solidifies quickly. This material was re-dissolved in ethyl acetate (75 mL). A solution of L-ditoluyl tartaric acid (11.3 g, 29 mmol) in ethyl acetate (75 mL) was added. Precipitation started within 5 minutes. Ethyl acetate (50 mL) was added and the mixture was stirred for 72 hours at room temperature. Solids were collected on a glass filter. Yield: 14.2 g. This material was treated with 2N NaOH (cold, 180 mL). The aqueous phase was extracted with ethyl acetate (3×200 mL). The organic phase was washed with 2 N NaOH (cold, 75 mL) then with water until washings were neutral (pH 7). The organic phase was dried (sodium sulphate) and concentrated. Yield: 6.7 g of S-Venlafaxine (compound 1) as white crystalline solid. m.p. 104.5° C.-106° C. $[\alpha]_D^{23}=+13.9$ (c=1.6, MeOH). Chiral HPLC: 98% e.e. $^1$H-NMR (CDCl$_3$): see above.

S-Venlafaxine N-oxide (compound 3) was prepared as follows:

Crude material (2.2 g, 7.5 mmol) has been obtained by FAI (106796), according to the procedure described for compound 4 below. Pure compound 3 was obtained by column chromatography (gradient dichloromethane:methanol, 9:1→dichloromethane: 3.5 M ammonia in methanol, 9:1). Yield: 1.70 g (5.8 mmol, 78%) of 3 as a slightly yellow solid. $[\alpha]_D^{23}=-20.8$ (c=1.0, MeOH). $^1$H-NMR (300 MHz, CDCl$_3$): δ 7.09 (d, 2H, J=8.5 Hz), 6.84 (d, 2H, J=8.5 Hz), 4.16 (m, 1H), 3.79 (s, 3H), 3.51 (dd, 1H, $^2$J=3.8 Hz, $^3$J=12.7 Hz), 3.41 (m, 1H) 3.27 (s, 3H), 3.07 (s, 3H), 1.78-1.60 (m, 3H), 1.60-1.35 (m, 4H), 1.29-1.01 (m, 2H), 0.95-0.76 (m, 1H).

R-Venlafaxine N-oxide (compound 4) was prepared as follows:

R-Venlafaxine (2, 1.0 g, 3.4 mmol) was dissolved in dichloromethane (60 mL). The solution was cooled to −10° C. m-CPBA (fresh, 2.9 g, 7.3 mmol) was added. The suspension was stirred for 30 min. at −10° C. TLC check revealed full conversion. K$_2$CO$_3$ (5.0 g, 36 mmol.) was added, and the mixture was stirred for 30 min. at 0° C. Dichloromethane (50 mL) was added and the suspension was filtered. The filtrate was dried and concentrated. The crude product was purified as above. Yield: 0.9 g (3.0 mmol, 90%) as a white solid. $[\alpha]_D^{23}$: not determined. $^1$H-NMR (300 MHz, CDCl$_3$): see above.

O-desmethyl-S-Venlafaxine (compound 5) was prepared as follows:

A solution of diphenylphosphine (18 mL, 0.1 mol) in dry tetrahydrofuran (120 mL) was, under N$_2$, cooled to −10° C. n-BuLi (2.5 M in hexanes, 50 mL) and additional tetrahydrofuran (40 mL) was added. The mixture was stirred for 30 min. at −10° C., then the temperature was allowed to raise to 0° C. At this temperature a solution of S-venlafaxine (1, 6.2 g, 23 mmol) in tetrahydrofuran (60 mL) was added. The mixture was stirred for 2 hours, while the temperature was allowed to raise to room temperature, and subsequently at reflux temperature for 16 hours.

The reaction mixture was cooled to room temperature, poured into 2N HCl (cold, 300 mL) and stirred for 10 min. The aqueous phase was washed (ethyl acetate, 3×300 mL), then neutralized (pH 7) by means of slow addition of NaHCO$_3$ (s), and extracted (ethyl acetate, 6×300 mL). The organic phase was dried (Na$_2$SO$_4$) and concentrated in vacuo. The residue was suspended in ethyl acetate (100 mL) and stirred for 30 min. Solids were collected on a glass filter, and washed with ethyl acetate, until the smell of diphenylfosfine could no longer be detected. Yield: 4.6 g (17.5 mmol, 76%). m.p. 237.3° C.-237.9° C. $[\alpha]_D^{23}=+17.0$ (c=0.88, MeOH). $^1$H-NMR (300 MHz, DMSO-d$^6$): δ 9.12 (br, 1H), 6.94 (d, 2H, J=8.3 Hz), 6.62 (d, 2H, J=8.3 Hz), 5.37 (br, 1H), 2.98 (m, 1H), 2.71 (t, 1H, J=5.8 Hz), 2.34 (m, 1H), 2.14 (s, 6H), 1.64-1.22 (m, 7H), 1.20-0.78 (m, 3H).

O-desmethyl-R-Venlafaxine (compound 6) was prepared as follows:

As above, starting with R-Venlafaxine (5.0 g, 18 mmol), using diphenylphosphine (14 mL) and n-BuLi in hexanes (2.5 M, 41 mL). Yield: 3.8 g (14.5 mmol, 80%). m.p. 235.5° C.-237.1° C. $[\alpha]_D^{23}=-21.3$ (c=0.9, MeOH). $^1$H-NMR (300 MHz, DMSO-d$^6$): see above.

O-desmethyl-S-venlafaxine N-oxide (compound 7) was prepared as follows:

O-desmethyl-S-Venlafaxine (5, 1.5 g, 5.7 mmol) was suspended in dichloromethane (100 mL). The suspension was cooled to −10° C. m-CPBA (4.8 g, 12 mmol) was added. The suspension was stirred for 60 min. at −10° C. TLC check revealed full conversion. K$_2$CO$_3$ (7.5 g, 54 mmol.) was added, and the mixture was stirred for 30 min. at 0° C. Dichloromethane (100 mL) was added and the suspension was filtered. The residue was stirred in methanol (300 mL), and filtered again. The combined filtrates were concentrated in vacuo (Yield: 7.1 g).

This material was purified by column chromatography. The crude product was dissolved in methanol (20 mL), brought on the column (silica in dichloromethane), eluted with dichloromethane (200 mL) and subsequently with dichloromethane: 7M NH$_3$ in methanol, 9:1. YIELD: 1.15 g (4.1 mmol, 72%) of compound 7 as a slightly yellow solid. $[\alpha]_D^{23}=-26.8$ (c=0.8, MeOH). $^1$H-NMR (300 MHz, DMSO-d$^6$): δ 9.66 (br, 1H), 6.98 (d, 2H, J=8.3 Hz), 6.69 (d, 2H, J=8.3 Hz), 3.88 (m, 1H), 3.55 (dd, $^2$J=2.4 Hz, $^3$J=12.7 Hz, 1H), 3.34 (br, 1H), 3.20 (dd, $^2$J=2.4 Hz, $^3$J=12.7 Hz, 1H), 3.14 (s, 3H), 2.95 (s, 3H), 1.69-1.20 (m, 6H), 1.11-0.66 (m, 4H).

O-Desmethyl-R-venlafaxine N-oxide (compound 8) was prepared as follows:

As above, starting with O-desmethyl-R-Venlafaxine (compound 6, 1.5 g, 5.7 mmol). Yield: 1.20 g (4.3 mmol, 75%) as a slightly yellow solid. $[\alpha]_D^{23}=+16.3$ (c=0.8, MeOH). $^1$H-NMR (300 MHz, DMSO-d$^6$): see above.

EXAMPLE 3

Pharmacological Methods

In vitro affinity for neurotransmitter reuptake sites were either obtained by CEREP (128, rue Danton, 92500 Rueil-Malmaison, France) or at Solvay Pharmaceuticals B. V. (C. J. van Houtenlaan 36, 1381 CP Weesp, The Netherlands), using well documented procedures. Measured were affinities for serotonin (Tatsumi, 1999), norepinephrine (Pacholczyk, 1991) and dopamine reuptake sites (Pristupa, 1994).

In vitro functional inhibition of [$^3$H]-serotonin reuptake: male rats (Wistar Hsd/Cpb: WU; 175-200 g) were decapitated, the cerebral hemispheres were rapidly removed, and a P2-synaptosomal fraction was prepared. Synaptosomes were pre-incubated in absence or presence of the test compound for 15 min at 37° C., in a medium containing the MAO inhibitor pargyline (7 µM). Subsequently, the synaptosomes were exposed to [$^3$H]-serotonin (0.2 mM final concentration) for 10 min. [$^3$H]-Serotonine uptake was stopped by filtration with a harvester and the non-incorporated radioactivity was removed by extensive washing. Filter plates with synaptosomes were dehydrated, and the amount of [$^3$H]-serotonin present was determined by Betaplate liquid scintillation counting. Inhibitory effects on the uptake of the [$^3$H]-serotonin were expressed as pIC$_{50}$ value, that is the negative logarithm of the concentration at which half maximal inhibition of radiolabeled neurotransmitter uptake is achieved. pIC$_{50}$ values given are mean values of 2-9 experiments performed in duplicate. Test compounds, 10$^{-2}$ M dissolved in DMSO, were diluted in Krebs Ringer buffer to the test concentrations of 10$^{-8}$ to 10$^{-5}$ M. Further experimental details were as described (Coyle, 1969).

In vitro functional inhibition of [$^3$H]-norepinephrine reuptake: male rats (Wistar Hsd/Cpb: WU; 175-200 g) were decapitated, the hypothalamus was rapidly removed and a crude synaptosomal fraction was prepared. Synaptosomes were pre-incubated in absence or presence of the test compound for 10 min at 37° C., in a medium containing the MAO inhibitor pargyline (7 µM). Subsequently, the synaptosomes were exposed to [$^3$H]-norepinephrine (0.4 mM final concentration) for 15 min. [$^3$H]-Norepinephrine uptake was stopped by filtration with a harvester and the non-incorporated radioactivity was removed by an extensive washing programme.

The filterplates with synaptosomes were dehydrated and the amount of [$^3$H]-norepinephrine present was determined by Betaplate liquid scintillation counting. Inhibitory effects on the uptake of the [$^3$H]-norepinephrine were expressed as pIC$_{50}$ value, that is the negative logarithm of the concentration at which half maximal inhibition of radiolabeled neurotransmitter uptake is achieved. pIC$_{50}$ values given are mean values of 2-9 experiments performed in duplicate. Test compounds, 10$^{-2}$ M dissolved in DMSO, were diluted in Krebs Ringer buffer to test concentrations of 10$^{-8}$-10$^{-5}$ M. Further experimental details were as described (Coyle, 1969).

In vitro functional inhibition of [$^3$H]-dopamine reuptake: male rats (Wistar Hsd/Cpb: WU; 175-200 g) were decapitated; the striatum was rapidly removed and a crude synaptosomal fraction (P2) was prepared by homogenization and centrifugation. Synaptosomes were pre-incubated in absence or presence of the test compound for 15 min at 37° C., in a medium containing the monoamine oxidase inhibitor pargyline (7×10$^{-6}$ M) (Coyle, 1969). Subsequently, [$^3$H]-dopamine (2×10$^{-7}$ M final concentration) was added and incubation was continued for 10 min. [$^3$H]-dopamine uptake was stopped by filtration and the synaptosomes were washed four times with phosphate buffered saline. The amount of [$^3$H]-dopamine in the synaptosomes was determined by Betaplate liquid scintillation counting. Compounds were tested in a concentration range of 10$^{-9}$ to 10$^{-5}$ M. Inhibitory effects on the uptake of [$^3$H]-dopamine were expressed using the pIC$_{50}$ value (the negative logarithm of the concentration at which the drug caused 50% uptake inhibition). Inhibition of DA uptake was performed in duplicate.

The human colon model TIM2 (TNO Intestinal Model 2): this model is a dynamic model for the human large intestine that simulates in vivo conditions. It is an artificial digestive system that has been validated by many studies (Minekus, 1999).

Venlafaxine-N-oxides are prodrugs of the parent compound. They are useful in the treatment of diseases effectively treatable—albeit with side effects—with venlafaxine such as depression, including major depressive disorder, generalized anxiety disorder, obsessive compulsive disorder, social anxiety disorder, panic disorder, general depressive disorders, diabetic neuropathy, migraine and vasomotor symptoms associated with menopause, also known as "hot flashes."

EXAMPLE 4

Pharmacokinetic and Pharmacological Test Results

Venlafaxine and its N-oxide, formulated in 40% HPβPCD or 1% methylcellulose, respectively, were individually administered (intravenously (i.v.) or orally (p.o.)) to male NMRI mice (3 animals per time point), after which their plasma and brain were analyzed by LC-MS (see method described above) for both compounds. Data was averaged (n=3), and the results are provided in Table 1 below.

TABLE 1

Plasma and brain concentrations of venlafaxine and its N-oxide.

| Administered | Time (h) | Venlafaxine Plasma [ng/ml] | Venlafaxine Brain [ng/g] | Venlafaxine-N-oxide Plasma [ng/ml] | Venlafaxine-N-oxide Brain [ng/g] |
|---|---|---|---|---|---|
| Venlafaxine 1.0 mg/kg i.v. | 0.17 | 250 | 710 | 0.32 | 0.19 |
| | 0.5 | 97 | 289 | 0.12 | 0 |
| | 1 | 49 | 200 | 0.10 | 0 |
| | 3 | 4.7 | 15 | 0 | 0 |
| | 7 | 0.30 | 1.7 | 0 | 0 |
| | 24 | 0.37 | 0 | 0 | 0 |
| Venlafaxine 10 mg/kg p.o. | 0.17 | 630 | 1133 | 2.5 | 0 |
| | 0.5 | 543 | 2267 | 7.0 | 0.37 |
| | 1 | 523 | 1800 | 3.0 | 0.09 |
| | 3 | 38 | 137 | 0.31 | 0 |
| | 7 | 3.6 | 15 | 0.06 | 0 |
| | 24 | 0 | 0 | 0 | 0 |
| Venlafaxine-N-oxide 1.0 mg/kg i.v. | 0.17 | 42 | 56 | 623 | 3.3 |
| | 0.5 | 22 | 52 | 173 | 58 |
| | 1 | 8.0 | 26 | 39 | 8.1 |
| | 3 | 0.59 | 3.0 | 7.3 | 0.44 |
| | 7 | 0 | 0.85 | 0.16 | 0.15 |
| | 24 | 0 | 0 | 0 | 0 |
| Venlafaxine-N-oxide 10 mg/kg p.o. | 0.17 | 82 | 55 | 1040 | 14 |
| | 0.5 | 72 | 167 | 840 | 33 |
| | 1 | 117 | 353 | 183 | 6.7 |
| | 3 | 77 | 280 | 38 | 1.8 |
| | 7 | 3.3 | 12 | 0.75 | 1.6 |
| | 24 | 0.63 | 0 | 0.12 | 0 |

In mice, venlafaxine is only marginally metabolized to its N-oxide. The concentration thereof in the plasma never exceeds 1-2% of that of the parent compound, and in brain only traces can be found. When venlafaxine-N-oxide itself is administered it is reduced to the parent compound. Approximately one hour after i.v. administration of venlafaxine-N-oxide, venlafaxine concentrations in plasma and brain exceed those of the N-oxide. The effects are more pronounced after oral administration; Venlafaxine concentrations in both plasma and brain rise to levels that are a factor 10 to 100 higher than those of the N-oxide.

Suspended in 1% methylcellulose, venlafaxine-N-oxide (1 mg) was inserted into the lumen (120 ml) of the TIM2 model (see above, Minekus, 1999). Samples from the lumen and the dialysate (the latter being a model for the vascular bed of the intestines) were taken at various time intervals, and analyzed for venlafaxine-N-oxide and venlafaxine. The results are provided in Table 2 below.

TABLE 2

Reduction of venlafaxine N-oxide in the human colon model TIM2.

| Time (h) | Venlafaxine-N-oxide Lumen [ng/ml] | Venlafaxine-N-oxide Dialysate [ng/ml] | Venlafaxine Lumen [ng/ml] | Venlafaxine Dialysate [ng/ml] |
|---|---|---|---|---|
| 0 | <1.0 | <1.0 | <1.0 | <1.0 |
| 2 | 2.0 | 7.4 | 5,400 | 320 |
| 4 | 2.0 | 1.2 | 4,700 | 470 |
| 6 | 2.0 | 1.0 | 4,600 | 430 |
| 8 | 1.9 | <1.0 | 3,900 | 370 |
| 24 | <1.0 | <1.0 | 970 | 210 |

From the results above, it is clear that already within 2 hours after dosing venlafaxine N-oxide was nearly quantitatively reduced to venlafaxine. Because many studies validated TIM2 as an in vitro model with high predictive value for the gastrointestinal conditions in living human beings, it is predicted that also in man, after oral administration, venlafaxine N-oxide will be reduced to venlafaxine. Thus, venlafaxine N-oxide is a prodrug.

TABLE 3

Plasma pharmacokinetics of venlafaxine and its N-oxide.

| | Venlafaxine | | Venlafaxine-N-oxide | |
|---|---|---|---|---|
| Route of administration: | i.v. | p.o. | i.v. | p.o. |
| Dose (mg/kg) | 1 | 10 | 1 | 10 |
| $C_{max}$ (ng/ml) | 407.9 $(C_0)$* | 630.0 | 1205.2 $(C_0)$* | 1040.0 |
| $T_{max}$ (hr) | 0.0 | 0.2 | 0.0 | 0.2 |
| $t_{1/2}$ (hr) | 0.8 | 0.9 | 0.8 | 3.1 |
| $AUC_{0 \to end}$ (ng/ml × hr) | 194.3 | 943.4 | 361.6 | 841.6 |
| → remark | $T_{end}$ = 24 hrs | $T_{end}$ = 7 hrs | $T_{end}$ = 7 hrs | $T_{end}$ = 24 hrs |
| $AUC_{0 \to \infty}$ (ng/ml × hr) | 194.8 | 948.0 | 361.7 | 842.2 |
| → remark | $T_{end} = \infty$ | $T_{end} = \infty$ | $T_{end} = \infty$ | $T_{end} = \infty$ |
| Clearance (ml/min/kg) | 85.6 | — | 46.1 | — |
| $V_D$ (ml/kg) | 6200.0 | — | 3000.0 | — |
| Bioavailability (%) | 48.7 | — | 23.3 | — |
| Brain/plasma ratio | 3.1 | 3.4 | 0.1 | 0.0 |

*For i.v. administration, $C_{max}$ values were extrapolated to $T_0$ (time zero)

From the data provided in Table 3 above, it is evident that clearance, volume of distribution and bioavailability of venlafaxine are twice as high as those of its pyridine N-oxide. Clearly, the two compounds have different pharmacokinetic properties. As is also clear from the data given in Table 1, venlafaxine-N-oxide hardly penetrates the brain: Hence, these compounds have dramatically different brain/plasma ratio's.

in vitro pharmacology of (O-desmethyl)venlafaxine, their N-oxides, and enantiomers

| | Dopamine | | Noradrenaline | | Serotonine | |
|---|---|---|---|---|---|---|
| Compound | binding $pK_i$ | inhibition $pIC_{50}$ | binding $pK_i$ | inhibition $pIC_{50}$ | binding $pK_i$ | inhibition $pIC_{50}$ |
| (R,S)-venlafaxine | 5.4 | 5.3 | 5.2 | 6.2 | 7.9 | 7.2 |
| (S)-venlafaxine | 4.8 | 5.0 | <4.5 | 6.1 | 8.0 | 7.3 |
| (R)-venlafaxine | 5.6 | 5.5 | 5.4 | 6.8 | 7.5 | 7.1 |
| (S)—O-desmethyl-venlafaxine | 4.9 | 5.0 | 4.6 | 6.4 | 8.0 | 7.3 |
| (R)—O-desmethyl-venlafaxine | 5.2 | 5.3 | 5.2 | 6.4 | 7.6 | 7.1 |
| (R,S)-venlafaxine-N-oxide | <4.5 | 4.5 | <4.5 | 4.9 | 5.5 | 4.9 |
| (S)-venlafaxine-N-oxide | <4.5 | <4.5 | <4.5 | <4.5 | 5.2 | 4.8 |
| (R)-venlafaxine-N-oxide | <4.5 | <4.5 | <4.5 | 4.4 | 5.1 | 4.7 |
| (S)—O-desmethyl-venlafaxine-N-oxide | <4.5 | <4.5 | <4.5 | <4.5 | 4.9 | 4.6 |
| (R)—O-desmethyl-venlafaxine-N-oxide | <4.5 | <4.5 | <4.5 | <4.5 | 5.0 | 4.4 |

The in vitro pharmacological data compiled in the table above clearly indicates that venlafaxine is most potent as inhibitor of serotonine reuptake. Its (R)- and (S)-enantiomers showed only marginal differences. The major metabolite, O-desmethylvenlafaxine, was found to be equipotent with venlafaxine, both as racemate, and in the form of its individual enantiomers.

The N-oxides of venlafaxine and O-desmethyl-venlafaxine, as racemates as well as individual (R)- or (S)-enantiomers were found to be virtually devoid of activity.

EXAMPLE 5

Pharmaceutical Preparations

For clinical use, N-oxide compounds of formula (1) are formulated into pharmaceutical compositions, which are novel embodiments of the invention because they contain the compounds, more particularly specific compounds disclosed herein. Types of pharmaceutical compositions that may be used include: tablets, chewable tablets, capsules (including microcapsules), solutions, parenteral solutions, ointments (creams and gels), suppositories, suspensions, and other types disclosed herein, or are apparent to a person skilled in the art from the specification and general knowledge in the art. The active ingredient for instance, may also be in the form of an inclusion complex in cyclodextrins, their ethers or their esters. The compositions are used for oral, intravenous, subcutaneous, tracheal, bronchial, intranasal, pulmonary, transdermal, buccal, rectal, parenteral or other ways to administer. The pharmaceutical formulation contains at least one N-oxide compound of formula (1) in admixture with at least one pharmaceutically acceptable adjuvant, diluent and/or carrier. In embodiments of the present invention, the total amount of active ingredients range of from about 0.1% (w/w) to about 95% (w/w) of the formulation, such as from 0.5% to 50% (w/w) and further for example, from 1% to 25% (w/w). In some embodiments, the amount of active ingredient is greater than about 95% (w/w) or less than about 0.1% (w/w).

The compounds of the invention can be brought into forms suitable for administration by means of usual processes using auxiliary substances such as liquid or solid, powdered ingredients, such as the pharmaceutically customary liquid or solid fillers and extenders, solvents, emulsifiers, lubricants, flavorings, colorings and/or buffer substances. Frequently used auxiliary substances include magnesium carbonate, titanium dioxide, lactose, saccharose, sorbitol, mannitol and other sugars or sugar alcohols, talc, lactoprotein, gelatin, starch, amylopectin, cellulose and its derivatives, animal and vegetable oils such as fish liver oil, sunflower, groundnut or sesame oil, polyethylene glycol and solvents such as, for example, sterile water and mono- or polyhydric alcohols such as glycerol, as well as with disintegrating agents and lubricating agents such as magnesium stearate, calcium stearate, sodium stearyl fumarate and polyethylene glycol waxes. The mixture may then be processed into granules or pressed into tablets. A tablet is prepared using the ingredients below:

| Ingredient | Quantity (mg/tablet) |
|---|---|
| venlafaxine N-oxide | 10 |
| Cellulose, microcrystalline | 200 |
| Silicon dioxide, fumed | 10 |
| Stearic acid | 10 |
| Total | 230 |

The components are blended and compressed to form tablets each weighing 230 mg.

The active ingredients may be separately premixed with the other non-active ingredients, before being mixed to form a formulation. The active ingredients may also be mixed with each other, before being mixed with the non-active ingredients to form a formulation.

Soft gelatin capsules may be prepared with capsules containing a mixture of the active ingredients of the invention, vegetable oil, fat, or other suitable vehicle for soft gelatin capsules. Hard gelatin capsules may contain granules of the active ingredients. Hard gelatin capsules may also contain the active ingredients together with solid powdered ingredients such as lactose, saccharose, sorbitol, mannitol, potato starch, corn starch, amylopectin, cellulose derivatives or gelatin.

Dosage units for rectal administration may be prepared (i) in the form of suppositories that contain the active substance mixed with a neutral fat base; (ii) in the form of a gelatin rectal capsule that contains the active substance in a mixture with a vegetable oil, paraffin oil or other suitable vehicle for gelatin rectal capsules; (iii) in the form of a ready-made micro enema; or (iv) in the form of a dry micro enema formulation to be reconstituted in a suitable solvent just prior to administration.

Liquid preparations may be prepared in the form of syrups, elixirs, concentrated drops or suspensions, e.g., solutions or suspensions containing the active ingredients and the remainder consisting, for example, of sugar or sugar alcohols and a mixture of ethanol, water, glycerol, propylene glycol and polyethylene glycol. If desired, such liquid preparations may contain coloring agents, flavoring agents, preservatives, saccharine and carboxymethyl cellulose or other thickening agents. Liquid preparations may also be prepared in the form of a dry powder, reconstituted with a suitable solvent prior to use. Solutions for parenteral administration may be prepared as a solution of a formulation of the invention in a pharmaceutically acceptable solvent. These solutions may also contain stabilizing ingredients, preservatives and/or buffering ingredients. Solutions for parenteral administration may also be prepared as a dry preparation, reconstituted with a suitable solvent before use.

Also provided according to the present invention are formulations and "kits of parts" comprising one or more containers filled with one or more of the ingredients of a pharmaceutical composition of the invention, for use in medical therapy. Associated with such container(s) can be various written materials such as instructions for use, or a notice in the form prescribed by a governmental agency regulating the manufacture, use or sale of pharmaceuticals products, which notice reflects approval by the agency of manufacture, use, or sale for human or veterinary administration. The use of formulations of the present invention in the manufacture of medicaments for use in treating depression, including major depressive disorder, generalized anxiety disorder, obsessive compulsive disorder, social anxiety disorder, panic disorder, general depressive disorders, diabetic neuropathy, migraine and vasomotor symptoms associated with menopause, also known as "hot flashes," and methods of medical treatment or comprising the administration of a therapeutically effective total amount of at least one N-oxide of formula (1), either as such or, in the case of prodrugs, after administration, to a patient suffering from depression, including major depressive disorder, generalized anxiety disorder, obsessive compulsive disorder, social anxiety disorder, panic disorder, general depressive disorders, diabetic neuropathy, migraine and vasomotor symptoms associated with menopause, also known as "hot flashes."

By way of example and not of limitation, several pharmaceutical compositions are given, comprising preferred active compounds for systemic use or topical application. Other compounds of the invention or combinations thereof, may be used in place of (or in addition to) said compounds. The concentration of the active ingredient may be varied over a wide range as discussed herein. The amounts and types of ingredients that may be included are well known in the art.

BIBLIOGRAPHY

To the extend in which the following references are useful to one skilled in the art, or to more fully describe this invention, they are incorporated herein by reference. Neither these, nor any other documents or quotes cited herein, nor citations to any references, are admitted to be prior art documents or citations.

Bickel, M. H.,: "*The pharmacology and Biochemistry of N-oxides*", Pharmacol. Reviews, 21(4), 325-355, 1969.

Bundgaard, H. (editor), "*Design of Prodrugs*", Elsevier, 1985.

Coyle, J. T. and S. H. Snyder, 1969, "*Catecholamine uptake by synaptosomes in homogenates of rat brain; stereospecificity in different areas*", J. Pharmacol. Exp. Ther. 170, 221-231, 1969.

Ettmayer, P. et al., "*Lessons learned from marketed and investigational prodrugs*", J. Med. Chem., 47, 2393-2404, 2004.

Howell, S. R. et al. Xenobiotica 24(4):315-327 (1994).

Janowsky, A. et al., J. Neurochem., 46, 1272-1276, 1986.

Järvinen, T. et al., "*Design and Pharmaceutical applications of prodrugs*", pages 733-796 in: S. C. Gad (editor): "*Drug Discovery Handbook*", John Wiley & Sons Inc., New Jersey, U.S.A., 2005.

King, F. D., (editor), page 215 in: "Medicinal Chemistry: Principles and Practice", 1994, ISBN 0-85186-494-5.

Klamerus, K. J. et al. J. Clin. Pharmacol. 32:716-724 (1992).

Minekus, M., M. Smeets-Peter, A. Bernalier, S. Marol-Bonnin, R. Havenaar, P. Marteau, M. Alric, G. Fonty, and J. H. J. Huis in't Veld. '*A computer-controlled system to simulate conditions of the large intestine with peristaltic mixing, water absorption and absorption of fermentation products*'. Appl. Microbiol. Biotechnol. 53:108-114, 1999.

Pacholczyk, T. et al., Nature, 350, 350-354, 1991

Pento, J. T. Drugs of the Future 13(9):839-840 (1988).

Physicians' Desk Reference pp. 3293-3302 (53rd ed., 1999).

Pristupa, Z. B. et al., Mol. Pharmacology., 45, 125-135, 1994.

Sinclair, J. et al. Rev. Contemp. Pharmacother. 9:333-344 (1998).

Stella, J., "*Prodrugs as therapeutics*", Expert Opin. Ther. Patents, 14(3), 277-280, 2004.

Tatsumi, M., et al., Eur. J. Pharmacol., 368, 277-283, 1999

Patents and Patent Applications
EP 1 721 889
U.S. Pat. No. 4,761,501

What is claimed is:

1. A compound of formula (1):

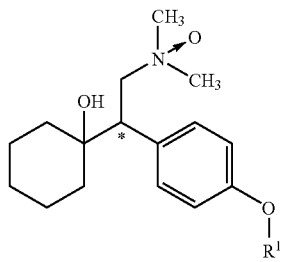

(1)

or a tautomer or stereoisomer thereof, wherein the asterisk (*) marks the asymmetric carbon atom, wherein $R^1$ is $CH_3$.

2. The compound as claimed in claim 1, wherein the compound is the (R)-enantiomer.

3. The compound as claimed in claim 1, wherein the compound is the (S)-enantiomer.

4. A medicament comprising a compound of formula (1):

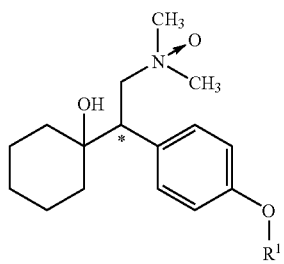

(1)

or a tautomer or stereoisomer thereof, wherein the asterisk (*) marks the asymmetric carbon atom, wherein $R^1$ is $CH_3$.

5. A pharmaceutical composition comprising, at least one pharmaceutically acceptable carrier, at least one pharmaceutically acceptable auxiliary substance, or a combination thereof, and at least one compound of formula (1):

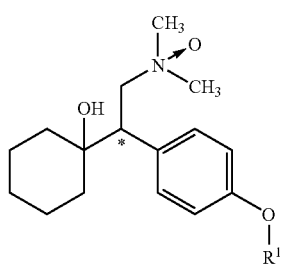

(1)

or a tautomer or stereoisomer thereof, wherein the asterisk (*) marks the asymmetric carbon atom, wherein $R^1$ is $CH_3$.

6. A combination pharmaceutical preparation comprising:
(i) a compound of formula (1):

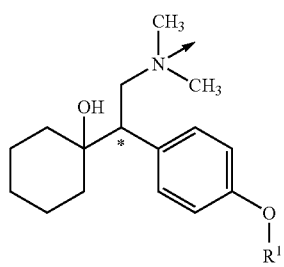

(1)

or a tautomer or stereoisomer thereof, wherein the asterisk (*) marks the asymmetric carbon atom, wherein $R^1$ is $CH_3$, and (ii) a second therapeutic agent, for simultaneous, separate or sequential use in treating a condition chosen from depression, major depressive disorder, generalized anxiety disorder, obsessive compulsive disorder, social anxiety disorder, panic disorder, general depressive disorders, diabetic neuropathy, migraine and hot flashes, wherein treating includes at least one of inhibiting the condition, relieving the condition, or stopping the symptoms of the condition.

7. The combination pharmaceutical preparation as claimed in claim 6, wherein said second therapeutic agent is venlafaxine or O-demethylvenlafaxine.

8. A method for treating a condition chosen from depression, major depressive disorder, generalized anxiety disorder, obsessive compulsive disorder, social anxiety disorder, panic disorder, general depressive disorders, diabetic neuropathy, migraine and hot flashes, said method comprising administering a composition comprising compound of formula (1):

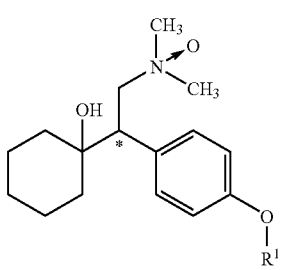

(1)

or a tautomer or stereoisomer thereof, wherein the asterisk (*) marks the asymmetric carbon atom, wherein $R^1$ is $CH_3$, in a human or animal patient in need of such treating, wherein treating includes at least one of inhibiting the condition, relieving the condition, or stopping the symptoms of the condition.

9. A process for preparing a pharmaceutical composition comprising:
(i) combining a compound of formula (1):

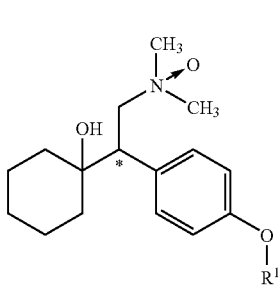

(1)

or a tautomer or stereoisomer thereof, wherein the asterisk (*) marks the asymmetric carbon atom, wherein $R^1$ is $CH_3$, with at least one pharmaceutically acceptable carrier, at least one pharmaceutically auxiliary substance, or a combination thereof; and (ii) formulating the combination produced in (i) into a suitable dosage form.

10. A process for preparing a combination preparation comprising:
(i) combining a compound of formula (1):

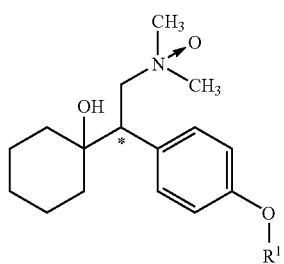

(1)

or a tautomer or stereoisomer thereof, wherein the asterisk (*) marks the asymmetric carbon atom, wherein $R^1$ is $CH_3$, a second therapeutic agent, and at least one pharmaceutically acceptable carrier, at least one pharmaceutically auxiliary substance, or a combination thereof; and
(ii) formulating the combination produced in (i) into a suitable dosage form.

11. A process for preparing a compound of formula (1):

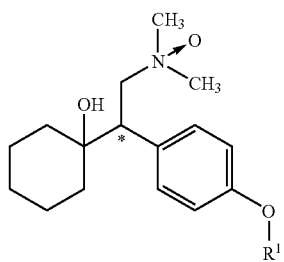

(1)

or a tautomer or stereoisomer thereof, wherein the asterisk (*) marks the asymmetric carbon atom, wherein $R^1$ is $CH_3$, the process comprising reacting a compound of formula (a) with an oxidizing agent:

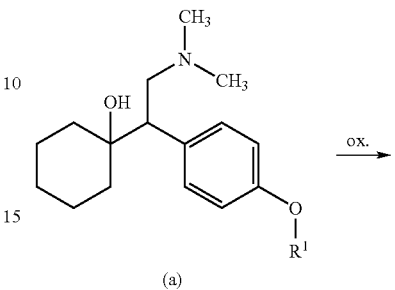

(a)

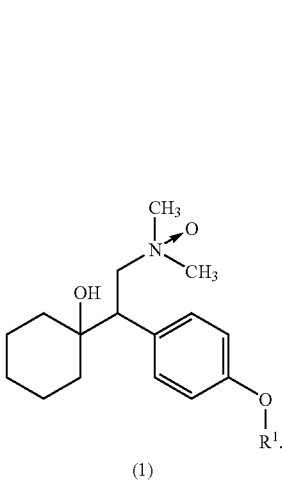

(1)

* * * * *

UNITED STATES PATENT AND TRADEMARK OFFICE
CERTIFICATE OF CORRECTION

PATENT NO. : 7,696,383 B2  Page 1 of 2
APPLICATION NO. : 12/143919
DATED : April 13, 2010
INVENTOR(S) : Turski et al.

It is certified that error appears in the above-identified patent and that said Letters Patent is hereby corrected as shown below:

On the Title Page, Item (75), in the Inventors, line 4, "Martinus Th. M. Tulp," should read --Martinus Th.M. Tulp,--.

On the Title Page, Item (57), in the Abstract, lines 6-7, "these compound," should read --these compounds,--.

In claim 6, column 21, lines 56-65,

" 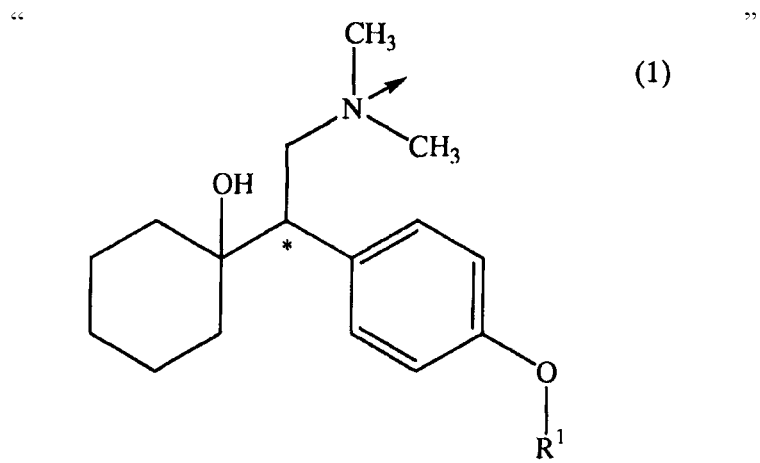 "  (1)

should read

Signed and Sealed this

Third Day of August, 2010

David J. Kappos
*Director of the United States Patent and Trademark Office*

CERTIFICATE OF CORRECTION (continued)
U.S. Pat. No. 7,696,383 B2

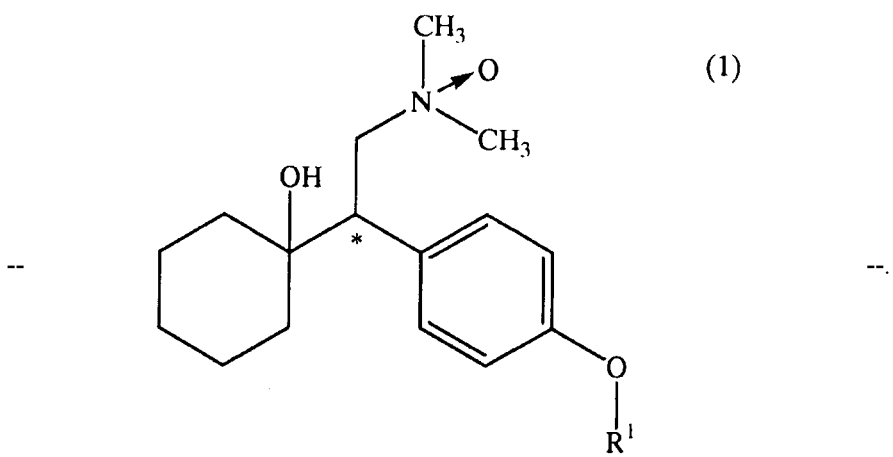

In claim 8, column 22, line 23, "comprising compound" should read --comprising a compound--.